United States Patent
Duncan

(10) Patent No.: US 9,364,638 B2
(45) Date of Patent: Jun. 14, 2016

(54) ADJUSTABLE VAGINAL ANCHOR FOR UTERINE TAMPONADE DEVICE AND METHODS OF USING THE SAME

(71) Applicant: Cook Medical Technologies LLC, Bloomington, IN (US)

(72) Inventor: Kate Duncan, Mooresville, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 227 days.

(21) Appl. No.: 14/160,141

(22) Filed: Jan. 21, 2014

(65) Prior Publication Data

US 2015/0202411 A1     Jul. 23, 2015

(51) Int. Cl.
| | |
|---|---|
| *A61M 29/02* | (2006.01) |
| *A61M 25/02* | (2006.01) |
| *A61M 25/04* | (2006.01) |
| *A61B 17/42* | (2006.01) |
| *A61B 17/12* | (2006.01) |
| *A61B 17/00* | (2006.01) |
| *A61M 25/10* | (2013.01) |

(52) U.S. Cl.
CPC .............. *A61M 25/04* (2013.01); *A61B 17/42* (2013.01); *A61B 17/12136* (2013.01); *A61B 2017/00557* (2013.01); *A61B 2017/4216* (2013.01); *A61M 29/02* (2013.01); *A61M 2025/1065* (2013.01)

(58) Field of Classification Search
CPC ..................... A61B 17/42; A61B 2017/12004
USPC .......................................................... 606/193
See application file for complete search history.

(56) References Cited

U.S. PATENT DOCUMENTS

| | | | | |
|---|---|---|---|---|
| 837,085 | A * | 11/1906 | Loar ................... | A61M 3/0291 604/108 |
| 4,043,338 | A * | 8/1977 | Homm .................. | A61M 31/00 604/105 |
| 4,430,076 | A | 2/1984 | Harris | |
| 4,552,557 | A | 11/1985 | Rangaswamy | |
| 5,338,297 | A * | 8/1994 | Kocur ................. | A61M 3/0295 604/103.03 |
| 5,613,950 | A * | 3/1997 | Yoon ................ | A61B 17/00234 600/225 |
| 5,935,098 | A * | 8/1999 | Blaisdell ................... | A61F 6/18 604/103.01 |

(Continued)

FOREIGN PATENT DOCUMENTS

| | | |
|---|---|---|
| FR | 3 003 472 | 3/2013 |
| WO | WO 02/28469 A1 | 4/2002 |

OTHER PUBLICATIONS

International Search Report and Written Opinion for PCT/US2015/011982, dated Apr. 1, 2015, 16 pp.

*Primary Examiner* — Susan Su
(74) *Attorney, Agent, or Firm* — Brinks Gilson & Lione

(57) ABSTRACT

A device for use with a uterine tamponade apparatus, such as the Bakri postpartum hemorrhage balloon, is disclosed. The device comprises an adjustable anchor for deployment within the vagina to securely retain the balloon in its proper position within the uterine cavity, allowing the balloon to function as intended for the control and management of postpartum hemorrhage and uterine bleeding. Methods of use of the vaginal anchor are also disclosed.

18 Claims, 3 Drawing Sheets

(56) References Cited

U.S. PATENT DOCUMENTS

| | | | |
|---|---|---|---|
| 6,017,359 A * | 1/2000 | Gershony | A61B 17/0057 606/192 |
| 6,024,753 A | 2/2000 | Claren et al. | |
| 6,277,138 B1 * | 8/2001 | Levinson | A61F 2/013 604/164.13 |
| 6,395,012 B1 * | 5/2002 | Yoon | A61B 17/00234 606/193 |
| 7,220,252 B2 | 5/2007 | Shah | |
| 7,347,866 B2 * | 3/2008 | Daignault | A61M 25/04 604/104 |
| 8,123,773 B1 | 2/2012 | Shirley | |
| 2001/0007945 A1 * | 7/2001 | Piraka | A61M 25/10 606/193 |
| 2002/0010457 A1 | 1/2002 | Duchon et al. | |
| 2003/0004462 A1 | 1/2003 | Halpin | |
| 2003/0130563 A1 | 7/2003 | Loy | |
| 2003/0236546 A1 | 12/2003 | Packer | |
| 2005/0149101 A1 | 7/2005 | Huschmand Nia | |
| 2005/0187561 A1 * | 8/2005 | Lee-Sepsick | A61B 17/42 606/108 |
| 2005/0267509 A1 * | 12/2005 | Davis | A61M 29/02 606/193 |
| 2006/0173486 A1 * | 8/2006 | Burke | A61B 17/12099 606/193 |
| 2006/0178692 A1 * | 8/2006 | Condrea | A61M 25/1027 606/192 |
| 2007/0232997 A1 | 10/2007 | Glenn | |
| 2008/0109010 A1 | 5/2008 | Feuer et al. | |
| 2008/0215031 A1 * | 9/2008 | Belfort | A61B 17/12099 604/500 |
| 2009/0048685 A1 | 2/2009 | Frigstad et al. | |
| 2009/0093758 A1 | 4/2009 | Gross | |
| 2011/0022073 A1 | 1/2011 | Gross et al. | |
| 2011/0087109 A1 | 4/2011 | Swann | |
| 2012/0053485 A1 | 3/2012 | Bloom | |
| 2013/0245581 A1 | 9/2013 | Norred et al. | |
| 2013/0253376 A1 * | 9/2013 | Juravic | A61B 17/42 600/588 |
| 2014/0303747 A1 * | 10/2014 | Clark | A61B 17/42 623/23.67 |

* cited by examiner

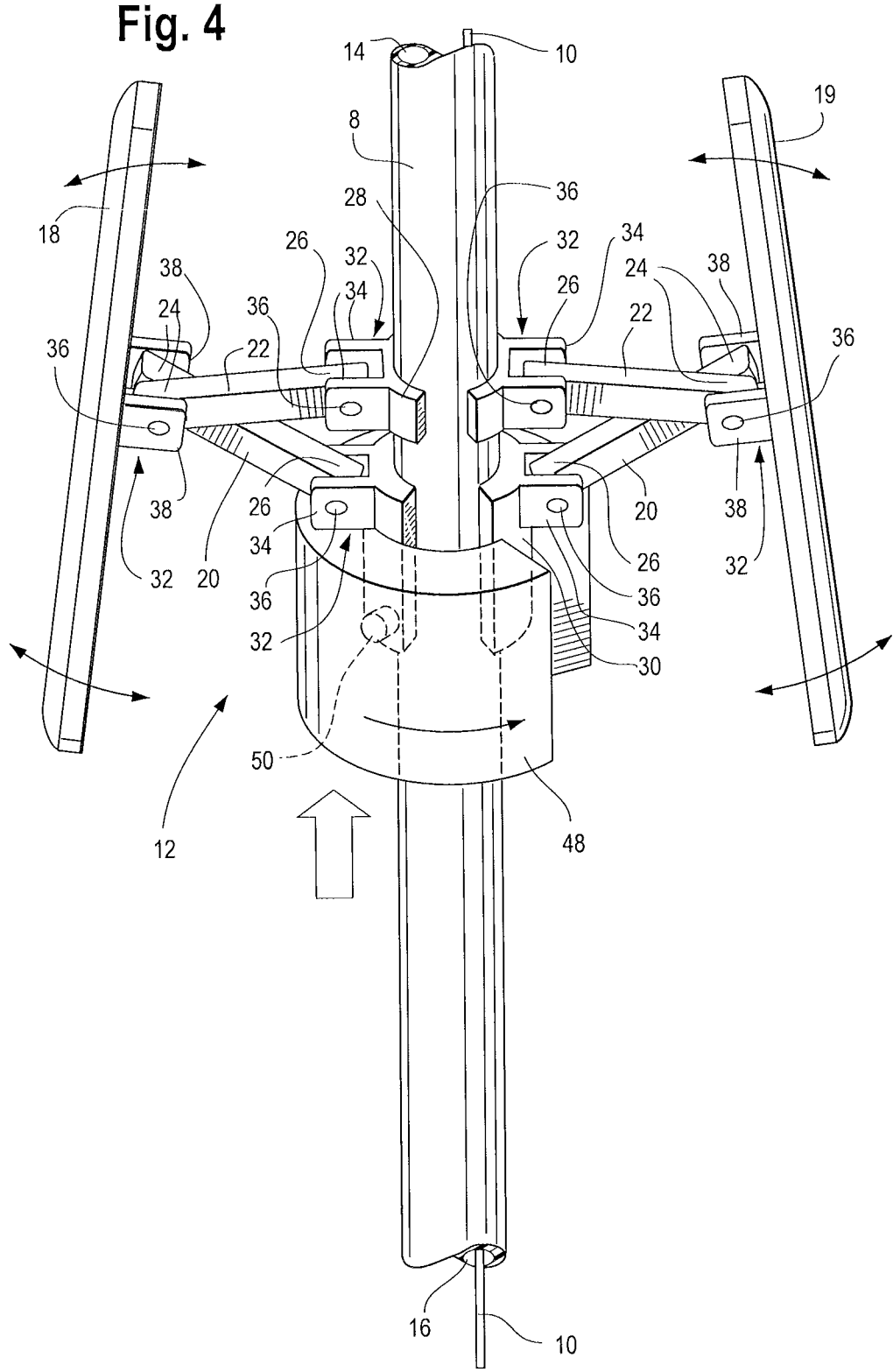

ADJUSTABLE VAGINAL ANCHOR FOR UTERINE TAMPONADE DEVICE AND METHODS OF USING THE SAME

TECHNICAL FIELD

The present invention relates generally to apparatus and methods for controlling uterine bleeding, and more specifically, to a retention mechanism for use with a uterine tamponade device that facilitates proper positioning and retention of the tamponade device within the uterus.

Uterine bleeding is a clinical condition attributable to a variety of causes, including postpartum hemorrhages (PPH) following vaginal and/or cesarean childbirth. Postpartum hemorrhage or excessive blood loss after birth is commonly caused by uterine atony whereby the uterus fails to contract normally after the delivery of a baby, leading to continuous bleeding. If left untreated, PPH may cause serious complications or even death.

There are a variety of techniques used for treating and managing PPH, including the administration of muscle contracting drugs or agents alone or in combination with other mechanical or surgical techniques. One such technique includes inserting a tamponade apparatus, such as a balloon catheter into the uterus, wherein the balloon is inflated to a sufficient pressure and volume until it conforms generally to the contour of the uterine cavity. The application of pressure to the interior uterine wall provides a tamponade effect until bleeding is controlled or stopped. One example of a uterine tamponade balloon catheter is the Bakri balloon, Cook Medical, Bloomington, Ind. The effectiveness of the Bakri balloon may be partially attributable to maintaining the balloon in a proper position within the uterine cavity, and more specifically, in the lower uterine segment.

In most cases, the balloon stays in place in the uterus during treatment as long as the balloon was inserted properly. However, in some instances, the uterus may try to "deliver" or expel the balloon through an insufficient or dilated cervix and into the vagina, thereby requiring the balloon to be deflated and reinserted. Thus, it is desirable to prevent full or partial dislodgement of the balloon from the uterus, by providing a device which anchors the balloon catheter in the uterus from a location within the vagina. Accordingly, the disclosed device can be used with various known uterine tamponade devices, such as the Bakri balloon. The disclosed device may be deployed within the vagina to securely retain the balloon in its proper position within the uterine cavity, allowing the balloon to function as intended for the control and management of PPH and uterine bleeding.

SUMMARY

The present disclosure provides an apparatus and method for securely anchoring a uterine tamponade device in its proper position within the uterine cavity. In one example, an apparatus for controlling hemorrhage in a body cavity is disclosed. The apparatus comprises a catheter comprising a longitudinal body having a proximal end and a distal end and at least one drainage lumen extending therebetween. An expandable tamponade device is located at the distal end of the catheter, the tamponade device configured for insertion into the body cavity. The apparatus further comprises a retention device for securing the apparatus within the body cavity, the retention device comprising at least one collar removably attached to the longitudinal catheter body, at least two arms moveable between a first radially contracted position and a second radially expanded deployed position and a locking mechanism for maintaining the arms in the deployed position.

An adjustable vaginal anchor for securing a balloon catheter in the uterine cavity is also disclosed. In one example, the anchor comprises a first collar and a second collar, the second collar being moveable between a first position longitudinally spaced from the first collar and a second position substantially adjacent to the first collar. The anchor further comprises first and second arms moveable between a first radially contracted position and a second radially expanded deployed position for engaging a vaginal wall, such that when the second collar is in the first position the arms are radially contracted and when the second collar is in the second position the arms are deployed. A locking collar is engageable with the second collar, the locking collar adapted to releasably secure the arms in the deployed position.

A method of retaining a tamponade balloon catheter in the uterine cavity is also disclosed. In one example, the method comprises attaching a retention device on a longitudinal shaft of a balloon catheter, the retention device comprising a first collar and a second collar, the second collar being moveable between a first position longitudinally spaced from the first collar and a second position substantially adjacent to the first collar; first and second arms moveable between a first radially contracted position and a second radially expanded deployed position for engaging a vaginal wall; and a locking collar engageable with the second collar, the locking collar adapted to releasably secure the arms in the deployed position. The method further comprises sliding the retention device longitudinally on the catheter shaft into a desired location within the vaginal canal with the second collar in the first position and the arms in the radially contracted position and then sliding the second collar distally on the longitudinal shaft to the second position, thereby deploying the arms to the second radially expanded position until the arms engage the vaginal wall. The locking collar may then be rotated to releasably secure the arms in the radially expanded deployed position.

BRIEF DESCRIPTION OF THE DRAWINGS

FIG. 4 is a perspective view of the retention device of FIG. 2 with the arms extended in a radially outward deployed position.

DETAILED DESCRIPTION

Throughout this specification, the terms proximal and proximally are used to refer to a position or direction away from, or even external to a patient's body and the terms distal and distally are used to refer to a position or direction towards the patient and/or to be inserted into a patient's body orifices or cavities. The embodiments described below are primarily in connection with a device for use with, or as an accessory to, a tamponade device such as a balloon catheter for treating postpartum hemorrhage, and for anchoring the balloon catheter in a desired position within the uterus. However, the described device may also be used in connection with a range of medical instruments which are inserted into various body cavities to maintain the position of such instruments depending on the technique or procedure being performed as will be appreciated by those of skill in the art.

Figure 1:
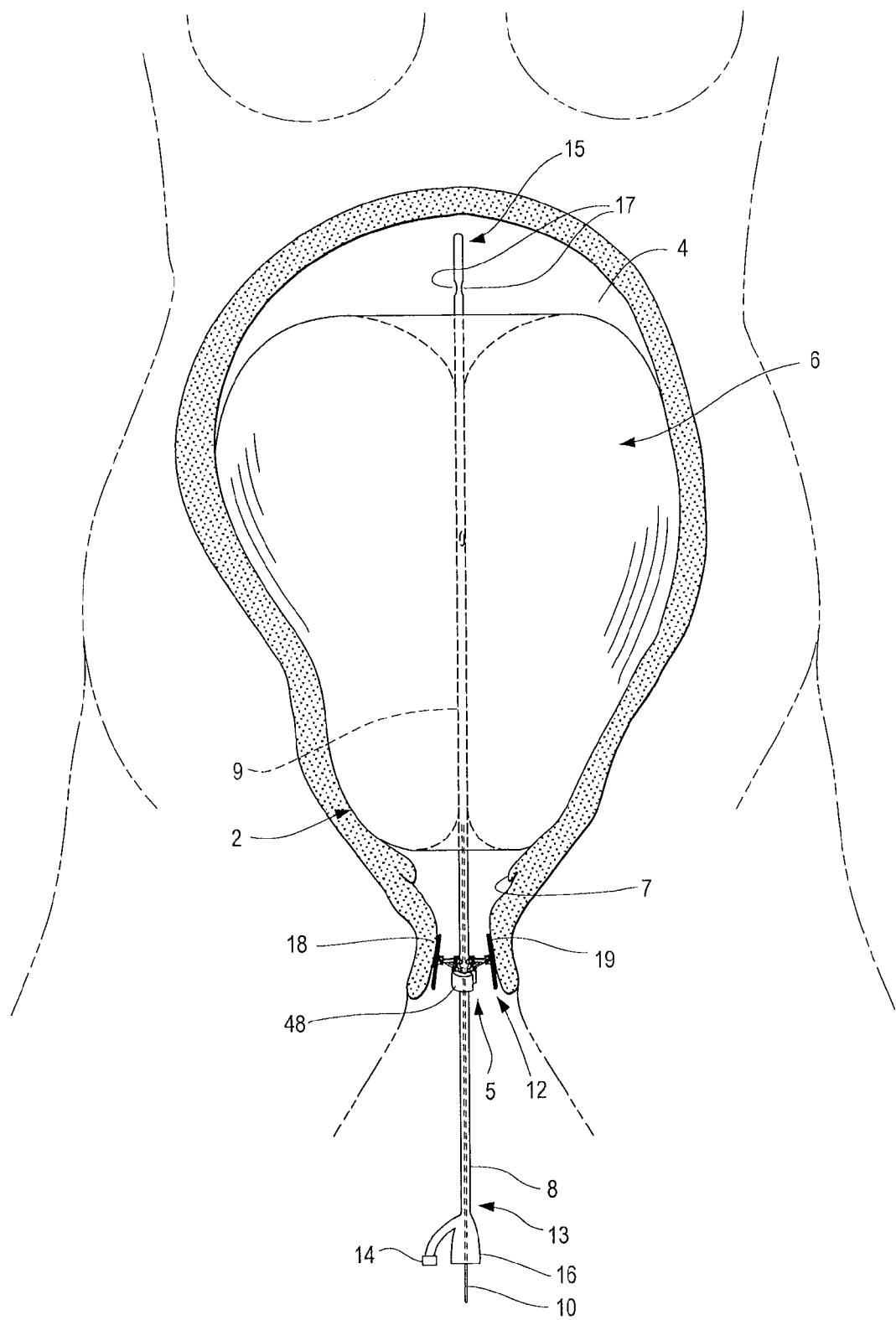
FIG. 1 is a front view of a patient's anatomy showing a uterine tamponade device and one example of retention device deployed in the vagina for anchoring the tamponade device in place within the uterine cavity.

FIG. 1 illustrates one example of a uterine tamponade assembly 2 positioned within a patient's anatomy. Tamponade, which is the closure or blockage of a wound by applying direct pressure to the source of bleeding, is a useful method of stopping or managing bleeding or hemorrhage. Once example of a known tamponade assembly includes a Bakri balloon catheter (Cook Medical, Bloomington, Ind.). The tamponade assembly 2, i.e., Bakri balloon catheter, is shown as being expanded within the uterine cavity and is shown as being equipped with a retention device 12 deployed in the vagina 5 for anchoring the balloon catheter 2 in place within the uterine cavity 4. While the balloon catheter 2 is intended for placement in the uterine cavity 4 of a patient for treating and controlling postpartum hemorrhage (PPH), it may also be used in various other locations, lumens or orifices within the body, including vessels, bones, organs or other tissues, as necessary or desired. Its dimensions are alterable so that it may be appropriately dimensioned to navigate to the uterus 4, or any other target body cavity, from which fluid, such as blood, will be drained. As shown in FIG. 1, the tamponade assembly 2 preferably includes a catheter 8 having a longitudinal body 9 and a distal end 15 and a proximal end 13. There is a drainage lumen 16 extending along the length of the longitudinal body 9 between the proximal 13 and distal 15 ends and, in one example, a connector (such as a Y-connector or any other suitable connector) may be located at the proximal end 13 of the catheter 8 for connecting the catheter to a collection bag or receptacle for receiving fluid and/or blood drained from the patient. The catheter 8 may include one or more openings 17 at or near its distal end 15, such that when the distal end 15 of the catheter 8 is positioned in the uterus 4, the openings 17 allow blood and other fluids to enter and flow through the drainage lumen 16. The drainage lumen may also be used to introduce irrigation fluid or other material into the uterus, such as to flush the openings 17 at the distal end 15 of the catheter 8 should they become blocked with clotted blood, tissue or other debris. The catheter 8 may also include additional ports or orifices at various points along the longitudinal body 9 to allow blood or other fluid to enter the catheter 8.

A tamponade device 6, such as a balloon, is located near the distal end 15 of the catheter 8, and is preferably made of an expandable material such as rubber, silicone, latex or any other expansible biocompatible material. Other tamponade mechanisms may also be used in lieu of or in addition to the balloon 6, such as plurality of arms, tubes, loops, mesh or similar structures capable of expanding or otherwise conforming to the uterine cavity 4. An inflation lumen 14 within the catheter 8 is provided to allow for inflation and deflation of the balloon 6. The inflation lumen 14 may run parallel with the drainage lumen 16, but preferably, the two lumens 16, 14 remain separate for their entire lengths. Various media, such as water, saline, air or other physiologically compatible medium may be introduced through the inflation lumen 14 to facilitate controlled expansion of the balloon 6.

Once the balloon 6 has been placed within the uterus 4 of the patient, the balloon 6 may be inflated or otherwise expanded. Preferably, the balloon 6 has sufficient compliance such that, when expanded, it conforms generally to the shape and contour of the cavity in which it is placed, and when deflated, can be sufficiently reduced in profile to provide for easy insertion and removal through the cervix 7 and vagina 5. The size and volume to which the balloon 6 may expand is preferably determined by the body cavity where hemorrhage control is needed. As shown in FIG. 1, the balloon 6 is preferably inflated with a sufficient volume and pressure such that it conforms generally to the contours of the uterine cavity 4, and more specifically, to the lower uterine segment. The inflated balloon 6 then exerts a generally uniform compressive force or pressure upon the uterine wall to substantially reduce or even stop the uterine bleeding or hemorrhage. It may also be possible to coat or impregnate all or at least a portion of the balloon surface that comes into contact with the uterine wall with biocompatible materials, drugs or other substances that may enhance or assist in controlling uterine bleeding. In one non-limiting example, this may include muscle contracting or clotting enhancing drugs or other substances that facilitate inflation/deflation of the balloon 6.

Figure 2:
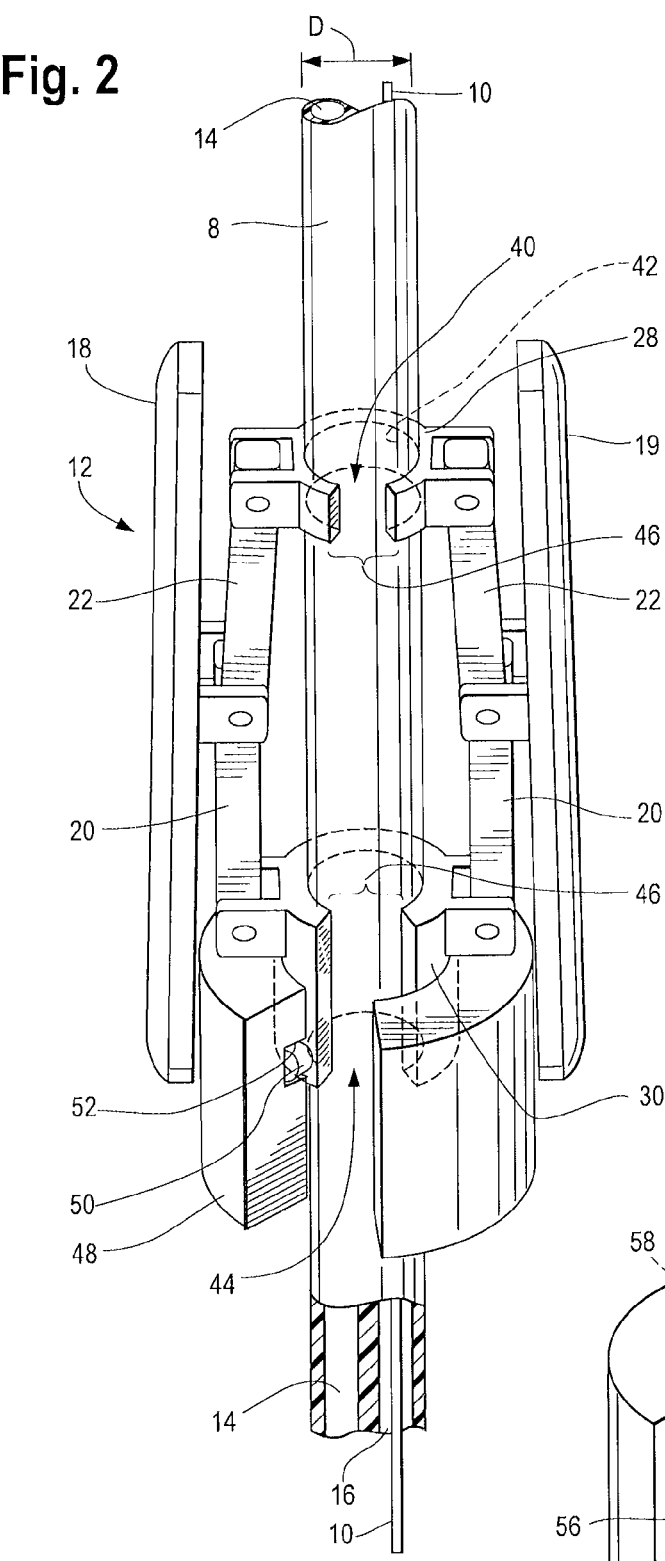
FIG. 2 is a perspective view of one example of a retention device secured to a catheter shaft with the arms in a radially constricted delivery position.

As shown in FIGS. 1, 2 and 4, the catheter 8 may further include an internal stylet 10 to provide structure or added rigidity to the catheter 8. The stylet 10 may be integrally formed within the catheter or, alternatively, the stylet 10 may be inserted into the catheter 8 by a physician prior to or during use. Preferably, the stylet 10 extends longitudinally within the drainage lumen 16, or alternatively through the inflation lumen 14 or through an additional or separate lumen. In one non-limiting example, the internal stylet 10 may be a hollow vinyl tube with a lumen extending there through, which provides an additional drainage conduit through which blood or other fluids can flow. However, the stylet 10 may be a variety of other shapes and configurations, solid or hollow, and made of suitable biocompatible materials including plastics, metals and/or combinations thereof. The stylet 10 may run the entire length, or at least a portion of the length of the catheter 8, and extend to a location adjacent to or just distal of the openings 17 at the distal end 15 of the catheter 8, for example, or at least extend a sufficient length so as to add longitudinal stability to the catheter 8. The stylet 10 thereby reduces or substantially eliminates unwanted folding and/or bending of the catheter 8, while also resisting and preventing longitudinal shortening, shrinkage and/or collapse during trans-vaginal insertion (and/or insertion through C-section) and during positioning of the balloon 6 within the uterus 4.

As illustrated generally in FIG. 1, the assembly 2 further includes a device 12 to facilitate retention of the assembly 2 and prevent unintentional or unwanted dislodgement once the balloon 6 has been properly positioned and expanded within the uterus 4. In one example, the device is retention mechanism such as expandable adjustable anchor 12. The anchor 12 is preferably usable in connection with the balloon catheter assembly 2, and may be provided as an accessory thereto. It is also contemplated that the anchor 12 may be used in connection with other medical devices in which it is desirable to retain such devices in a particular position or location within a body cavity. As such, the anchor 12 is preferably removably attachable to the assembly 2 so that it can be attached or secured to the catheter 8 when needed, and also conveniently removed if desired. In one example, the anchor 12 can be snap-fitted onto the longitudinal catheter body 9 at a desired location, or otherwise removably attached such as by friction fit, adhesive or other suitable attachment mechanisms, while allowing the anchor 12 to remain slideably movable along the longitudinal body 9 of the catheter 8.

When deployed, the retention mechanism 12 will expand radially outwardly and apply force to the vaginal wall, thus fixing the catheter shaft 9 and balloon 6 in place and substantially prevent dislodgement of the balloon 6 from the uterus 4. As previously noted, the rigidity provided to the catheter 8 by the internal stylet 10 prevents longitudinal collapse of the catheter 8, such that at least the portion of the catheter 8 located between the balloon 6 and the retention mechanism 12 will maintain structural integrity and longitudinal length.

This prevents longitudinal shrinkage or collapse of the longitudinal catheter body 9 when force is exerted on it in either a proximal and/or distal direction, such as in the event that the uterus 4 attempts to "deliver" the balloon 6 through an insufficient cervix (thus exerting pressure on the catheter body 9 in a proximal direction) and/or when a physician pushes the catheter 8 into the uterus 4 during insertion (thus exerting pressure on the catheter body 9 in a distal direction).

One example of the retention mechanism, such as anchor 12, is shown in FIGS. 2 and 4. As illustrated there, the anchor 12 preferably comprises at least two arms 18, 19 which are adjustable between a radially outward deployed position for engaging the vaginal wall as shown in FIG. 4, and a radially constricted delivery position as shown in FIG. 2. The arms 18, 19 may be approximately 6 cm long and 1.5 cm wide, although other shapes and dimensions are possible depending on various factors including the location of deployment and the particular anatomy of the patient. Each arm 18, 19 is attached to at least one, and preferably a pair of rods 20, 22. The rods 20, 22 each include a first end 24 and a second end 26. The first end 24 of each of the rods 20, 22 is attached to one arm 18, 19. The second end 26 of one of the rods 20, 22 is attached to a top collar 28, and the second end 26 of the other of the rods 20, 22 is attached to a bottom collar 30. The rods 20, 22 may be secured to the arms 18, 19 and also secured to the top and bottom collars 28, 30, respectively, by various means which allow relative movement among the arms 18, 19, rods 20, 22 and collars 28, 30, thus allowing the arms 18, 19 to be adjusted and moved between the radially outward deployed position (FIG. 4) and radially constricted delivery position (FIG. 2).

More particularly, each pair of rods 20, 22 may be attached, at one end 24 to one of the arms 18, 19 by one or more hinges 32, while the opposing end 26 of the rods 20, 22 may also be attached to the top and bottom collars 28, 30, respectively, by one or more hinges 32. As FIGS. 2 and 4 show, the hinges 32 may be formed by pins 36 which extend through flanges 34 on the respective top and bottom collars 28, 30 and into one end 26 of the rods 20, 22, and another pin 36 which extends through the other end 24 of the rods 20, 22 and into flanges 38 on the respective arms 18, 19. However, the arms 18, 19, rods 20, 22 and collars 28, 30 may be attached by various other hinged means that allows them to be movable with respect to each other so that the arms 18, 19 can be adjusted, as needed between the extended and retracted positions. In one non-limiting example, the arms 18, 19 of the anchor 12 can be adjusted anywhere from 3 cm in the retracted position up to approximately 10 cm in the deployed position, although this may vary from one patient to another and also depend on the location of deployment.

As best shown in FIG. 2, the top collar 28 defines an opening or aperture 40 having an inner diameter of about 0.300 inches to about 0.320 inches or just large enough of a diameter to accommodate the outer diameter (D) of the catheter body shaft 9 which, as shown in FIG. 2 extends though the opening 40. The inner surface 42 of the opening 40 of the top collar 28 may further include one or more bumps, barbs, adhesives or sticky/tacky structures, made from rigid plastic, soft polymer, silicone or the like, which provide traction, thus resulting in an enhanced grip of the top collar 28 upon the catheter shaft 9. The traction serves to prevent unwanted and/or unintentional sliding of the top collar 28 along the catheter shaft 9. In other words, a physician may push the anchor 12 to manually slide it longitudinally along the catheter shaft 9, which requires the physician to use a pushing force that is sufficient to overcome the traction or grip of the top collar 28 on the catheter. However, the traction provided on the inner surface 42 of the top collar 28 for gripping the catheter shaft 9 is sufficient to prevent the anchor 12 from sliding longitudinally along the catheter 8 by itself, without the intentional manual force of the user. This ensures that the anchor 12 remains in place at a desired position on the catheter 8 both before it is deployed and also after it has been slideably pushed into place within the vagina 5 and/or after the arms have been extended in the deployed position as shown in FIG. 4.

The bottom collar 30 also defines an opening 44 having an inner diameter that is the same or similar to the diameter of opening 40 of the top collar 28, for snugly engaging the catheter shaft 9. The bottom collar opening 44 may optionally also include a surface for enhancing traction as described above with respect to the top collar 28. Each of the top and bottom collars 28, 30 also preferably include a space or cut-out 46 that allows the collars to be removably attached to the catheter 8, such as by snap-fitting over and at least partially around the catheter shaft 9 from the side. Alternatively, the openings 40, 44 in the respective collars 28, 30 may completely encircle the catheter 8, in which case they may be threaded onto one end of the catheter and pushed longitudinally to a desired location thereon for use.

Figure 3:
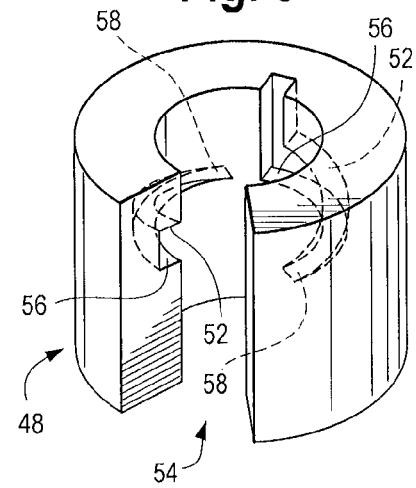
FIG. 3 is one example of a locking collar for the retention device shown in FIG. 2.

As illustrated in FIGS. 2-4, the bottom collar 30 mates with a locking collar 48 located just proximal of the bottom collar 30. The bottom collar 30 includes at least one, and preferably two, opposing protrusions or pegs 50 that extend from an outer surface of the bottom collar 30. The respective pegs 50 are each configured to be slideably engaged within a corresponding channel 52 formed in an inner surface of the locking collar 48. Each channel 52 is preferably formed in a single plane and extends at least partially around the circumference of the inner surface of the locking collar 48. In one example, as illustrated in FIG. 3, the channel 52 is gradually sloped and decreases in depth from about 5 mm at its deepest point where it originates at the two locations 56, and gradually becomes more shallow to about 1 mm where it terminates at locations 58. Interference between each of the protrusions 50 extending from the bottom collar 30 and slideably engaged within the respective channels 52 in the locking collar 48 increases as the locking collar 48 is rotated (e.g., clockwise) by the user due to the protrusions 50 engaging, such as by friction fit, with the decreasing depth of the channel 52 during rotation. When the locking collar 48 is fully rotated, the protrusions 50 are tightly engaged or "locked" with the surface of the most shallow portion 58 of the channel 52. Rotation of the locking collar 48 in the opposite direction (i.e., counter clockwise) allows the protrusions 50 to slide back towards the deeper portion 56 of the channel 52, thus releasing the lock.

The arms 18, 19, rods 20, 22 and collars 28, 30, 48 may be formed or molded from a rigid or semi-rigid plastic, for example including, but not limited to nylon, although other suitable materials may be used. These various components, and preferably the arms 18, 19, may also be over-molded or covered with a softer material, such as polyurethane to make them less traumatic to the sensitive tissue of the cervix 7 and vagina 5.

Turning now to FIGS. 1, 2 and 4, use and deployment of the retention device or "anchor" 12 with a uterine tamponade apparatus 2 such as the Bakri balloon catheter may be as follows. Before the uterine tamponade assembly 2 is inserted into a patient, the anchor 12 may be snap fitted on to the longitudinal catheter body 9 at a location that will, at least initially, remain outside of the patient. The internal stylet 10 may be inserted into a lumen of the catheter 8, such as into the drainage lumen 16. The distal end 15 of the catheter 8 carrying the tamponade balloon 6 may be inserted trans-vaginally through the cervix 7 (or alternatively inserted through C-section) and into the uterus 4 of a patient in its deflated or radially contracted state. Once the balloon 6 is in its desired position in the uterus 4, it is inflated or otherwise expanded with a physiologically suitable fluid through the inflation lumen 14. The shape of the fully expanded balloon will generally conform to the shape of the interior of the uterus 4, and preferably the lower uterine segment, thus exerting a compressive force against the uterine walls.

The anchor 12 may then be pushed in a distal direction along the catheter shaft 9 and into the vagina 5, in its radially constricted delivery position as shown in FIG. 2. Once the anchor 12 is properly located within the vagina 5, the physician may grip the locking collar 48 with a thumb and forefinger, push it in a distal direction, thus sliding the bottom collar 30 with it towards the top collar 28 until the top and bottom collars 28, 30 are closer together. In one example, top and bottom collars 28, 30 are substantially adjacent or may even abut each other as shown in FIG. 4 when the arms are fully extended radially outwardly. The top collar 28 remains in place on the catheter 8 due to the traction provided by the enhanced traction of the surface 42 such that movement of the bottom collar 30 and locking collar 48 towards the top collar 28 does not necessarily also cause unintentional sliding of the top collar 28 along the catheter body 9 in a distal direction. As the physician continues to push distally on the locking collar 48, thus sliding the bottom collar 30 towards the top collar 28, the arms 18, 19 extend radially outwardly until they contact the vaginal wall. The anchor 12 is therefore adjustable and/or customizable, in that the arms 18, 19 may deploy radially outwardly a selected distance so that they can be adjusted to fit with a variety of vaginal diameters depending on a particular patient's anatomy and location of deployment.

Once the deployed arms 18, 19 have achieved the desired force against the vaginal wall as determined by the physician, the locking collar 48 can be rotated over the bottom collar 30. Rotation of the locking collar allows the protrusions 50 on the bottom collar 30 become tightly engaged with the most shallow portion 58 of the channel 52 thus causing the bottom collar 30 to clamp down on or otherwise engage the outer surface of the catheter 8. The anchor 12, with the arms 18, 19 deployed within the vagina 5 and applying force to the vaginal wall, is thus "locked" in place in the deployed position within the vagina. In this way, the balloon 6 is retained in its proper position within the uterine cavity 4 by the anchor 12 resisting and even preventing displacement or dislodgement of the catheter 8 and the balloon 6 carried on the distal end thereof, allowing the apparatus 2 to function as intended for the control and management of PPH and uterine bleeding. Blood or other fluids within the uterus 4 may enter the openings 17 at the distal end 15 of the catheter 8 and drain though the drainage lumen 16 and/or the lumen of the stylet 10. The anchor 12 does not obstruct visualization of the cervix 7 and vagina 5 which allows continued monitoring of the tissues so that the physician may determine whether the bleeding has been controlled or stopped.

When release and removal of the anchor 12 is desired, the physician may rotate the locking collar 48 in the opposite direction so that the protrusions 50 slide back towards the deeper portion 56 of the channel 52, thus releasing the lock. The physician may then grip the locking collar 48 and slide it backwards in a proximal direction along the catheter shaft 9, thus moving the bottom collar 30 away from the top collar 28 so that the arms 18, 19 return to a radially contracted position as illustrated in FIG. 2. In the contracted position, the top and bottom collars 28, 30 may be separated by a distance of approximately 2.5-3.0 cm on the catheter shaft 9 as shown in FIG. 2. The physician may then pull the anchor 12 proximally along the catheter shaft 9 and withdraw it from the vagina 5. If and when uterine bleeding is controlled, the balloon 6 may then be deflated and withdrawn from the uterus 4.

Throughout this specification, unless the context requires otherwise, the words "comprise" and "include" and variations such as "comprising" and "including" will be understood to imply the inclusion of an item or group of items, but not the exclusion of any other item or group items.

While various embodiments of the invention have been described, it will be apparent to those of ordinary skill in the art that many more embodiments and implementations are possible within the scope of the invention. Furthermore, although various indications have been given as to the scope of this invention, the invention is not limited to any one of these but may reside in two or more of these combined together. Accordingly, the invention is not to be restricted except in light of the attached claims and their equivalents.

The invention claimed is:

1. An apparatus for controlling hemorrhage in a body cavity comprising:
   a catheter comprising a longitudinal body having a proximal end and a distal end and at least one drainage lumen extending therebetween;
   an expandable tamponade device located at the distal end of the catheter, the tamponade device configured for insertion into the body cavity;
   a retention device for securing the apparatus within the body cavity, the retention device comprising at least one collar slidably movable along the longitudinal catheter body, the at least one collar comprising a top collar having an inner surface adapted for engagement with the catheter longitudinal body, and a bottom collar located proximal to the top collar and spaced from the top collar, and first and second arms that are connected to the top and bottom collars, respectively, the first and second arms both moveable between a first radially contracted position and a second radially expanded position and a locking mechanism for maintaining the first and second arms in the expanded position.

2. The apparatus of claim 1 wherein the tamponade device comprises an inflatable balloon configured for expansion within a body cavity.

3. The apparatus of claim 1 wherein the body cavity comprises a uterine cavity.

4. The apparatus of claim 1 wherein the retention device is configured for insertion and expansion in the vaginal canal.

5. The apparatus of claim 1 further comprising a stylet extending longitudinally within the drainage lumen of the catheter.

6. The apparatus of claim 5 wherein the stylet comprises a proximal end and a distal end and a lumen extending therebetween.

7. The apparatus of claim 1 wherein at least a portion of the inner surface comprises a gripping surface adapted to enhance traction between the inner surface of the top collar and the catheter longitudinal body.

8. The apparatus of claim 1 wherein the top collar and bottom collar each define an opening having an inner diameter of approximately 0.300 inches to approximately 0.320 inches.

9. The apparatus of claim 1 wherein the locking mechanism is engageable with the bottom collar.

10. The apparatus of claim 9 wherein the locking mechanism comprises at least one channel and wherein the bottom collar further comprises at least one protrusion slideably engaged within the channel.

11. The apparatus of claim 1, wherein the at least one collar is frictionally attachable to the longitudinal catheter body, and is removable when the locking mechanism is disengaged from at least one collar.

12. An adjustable vaginal anchor for securing a balloon catheter in the uterine cavity comprising:
   a first collar,
   a second collar moveable between a first position longitudinally spaced from the first collar and a second position substantially adjacent to the first collar;
   first and second arms moveable between a first radially contracted position and a second radially expanded position for engaging a vaginal wall, such that when the second collar is in the first position the arms are radially contracted and when the second collar is in the second position the arms are expanded;
   a locking collar engageable with the second collar, the locking collar adapted to releasably secure the arms in the expanded position.

13. The vaginal anchor of claim 12 further comprising a first rod extending between the first collar and the first arm a second rod extending between the second collar and the first arm.

14. The vaginal anchor of claim 13 further comprising a third rod extending between the first collar and the second arm and a fourth rod extending between the second collar and the second arm.

15. The vaginal anchor of claim 13 wherein the first and second rods are hingedly connected to the first arm.

16. The vaginal anchor of claim 14 wherein the third and fourth rods are hingedly connected to the second arm.

17. An apparatus for controlling hemorrhage in a body cavity comprising:
   a catheter comprising a longitudinal body having a proximal end and a distal end and at least one drainage lumen extending therebetween;
   an expandable tamponade device located at the distal end of the catheter, the tamponade device configured for insertion into the body cavity;
   a retention device for securing the apparatus within the body cavity, the retention device comprising at least one collar removably attached to the longitudinal catheter body, at least two arms moveable between a first radially contracted position and a second radially expanded position and a locking mechanism for maintaining the arms in the expanded position;
   further comprising a stylet extending longitudinally within the drainage lumen of the catheter wherein the stylet comprises a proximal end and a distal end and a lumen extending therebetween.

18. A method of retaining a tamponade balloon catheter in the uterine cavity comprising:
   attaching a retention device on a longitudinal shaft of a balloon catheter, the retention device comprising a first collar; a second collar moveable between a first position longitudinally spaced from the first collar and a second position substantially adjacent to the first collar; first and second arms moveable between a first radially contracted position and a second radially expanded position for engaging a vaginal wall; and a locking collar engageable with the second collar, the locking collar adapted to releasably secure the arms in the expanded position;
   sliding the retention device longitudinally on the catheter shaft into a desired location within the vaginal canal with the second collar in the first position and the arms in the radially contracted position;
   sliding the second collar distally on the longitudinal shaft to the second position, thereby expanding the arms to the second radially expanded position until the arms engage the vaginal wall;
   rotating the locking collar to releasably secure the arms in the radially expanded position.

\* \* \* \* \*